US009095142B2

(12) United States Patent
Gu

(10) Patent No.: US 9,095,142 B2
(45) Date of Patent: Aug. 4, 2015

(54) LIGNIN DERIVATIVES HAVING POLYCATIONS AND USES THEREOF

(75) Inventor: Yansong Gu, Bellevue, WA (US)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 40 days.

(21) Appl. No.: 13/812,402

(22) PCT Filed: Jun. 28, 2012

(86) PCT No.: PCT/US2012/044547
§ 371 (c)(1),
(2), (4) Date: Jan. 25, 2013

(87) PCT Pub. No.: WO2014/003753
PCT Pub. Date: Jan. 3, 2014

(65) Prior Publication Data
US 2014/0005129 A1  Jan. 2, 2014

(51) Int. Cl.
A01N 65/00  (2009.01)
C07G 1/00  (2011.01)
A01N 25/34  (2006.01)
A01N 43/90  (2006.01)

(52) U.S. Cl.
CPC ............. A01N 65/00 (2013.01); A01N 25/34 (2013.01); A01N 43/90 (2013.01); C07G 1/00 (2013.01)

(58) Field of Classification Search
CPC ....... A01N 65/00; A01N 43/90; A01N 25/34; C07G 1/00
USPC .................................. 514/22; 530/500, 505
See application file for complete search history.

(56) References Cited

U.S. PATENT DOCUMENTS

| 2,429,102 | A | 10/1947 | Lewis et al. |
|---|---|---|---|
| 3,813,236 | A | 5/1974 | Allen et al. |
| 5,512,276 | A | 4/1996 | Lang et al. |
| 6,541,038 | B1 | 4/2003 | Tanaka et al. |
| 6,551,608 | B2 | 4/2003 | Yao |
| 6,727,347 | B1 | 4/2004 | Szego |
| 2003/0017565 | A1 | 1/2003 | Echigo et al. |
| 2003/0055007 | A1 | 3/2003 | Sakuma |
| 2009/0044292 | A1 | 2/2009 | Tien et al. |
| 2009/0208366 | A1 | 8/2009 | Subramanian |
| 2010/0124441 | A1 | 5/2010 | Ariyoshi et al. |
| 2010/0240592 | A1 | 9/2010 | Demarco et al. |
| 2010/0254900 | A1 | 10/2010 | Campbell et al. |
| 2010/0256089 | A1 | 10/2010 | Maguire et al. |
| 2010/0260813 | A1 | 10/2010 | Schnabel et al. |
| 2011/0027394 | A1 | 2/2011 | McClements et al. |
| 2011/0117176 | A1 | 5/2011 | Klun et al. |
| 2011/0294928 | A1* | 12/2011 | Nodera et al. .................. 524/73 |
| 2013/0236630 | A1* | 9/2013 | Brizius ........................ 427/2.12 |

FOREIGN PATENT DOCUMENTS

| EP | 2 199 046 A1 | 6/2010 |
|---|---|---|
| IN | WO 2010/074228 | * 1/2010 |
| WO | WO-2010/074228 | 7/2010 |

OTHER PUBLICATIONS

Najjar et al., Title: Zwitterionic lignin derivatives for marine antifouling; Probiotics and Antimicrobial Proteins, vol. 1, issue 2, pp. 143-147, published Dec. 2009 by Springer.*
Garrote, et al.; Title: Antioxidant activity of byproducts from the hydrolytic processing of selected lignocellulosic materials; Trends in Food Science & Technology; vol. 15, Issues 3-4, pp. 191-200, publishe Sep. 2003.*
Freundlich, J.S., et al. "Synthesis, biological activity, and X-ray crystal structure analysis of diaryl either inhibitors of malarial enoyl acyl carrier protein reductase. Part 1: 40-Substituted tricolsan derivaties," Bioorg. Med. Chem. Lett., 2005, 15, 5247-5252.
Sanches-Silva, A., et al., "Determination of triclosan in foodstuffs," J. Sep. Sci., 2005, 28, 65-72.
Schroeder, M., et al., "Enzymatic coating of lignocellulosic surfaces with polyphenols," Biotechnol. J., 2007, 2, 334-341.
US Office Action on U.S. Appl. No. 13/738,424 DTD Jun. 17, 2013.
US Notice of Allowance on U.S. Appl. No. 13/738,424 DTD Jul. 18, 2013.
Akiyama et al., "Antibacterial action of several tannins against *Staphylococcus aureus*," Journal of Antimicrobial Chemotherapy, 2001, vol. 48, Issue 4, pp. 487-49.
American Association of Textile and Color Chemists (AATCC), Test Method 100-1993, AATCC Technical Manual, 1997, pp. 143-144.
Binh N., et al. "Synthesis of Lignin-Based Thermoplastic Copolyester Using Kraft Lignin as a Macromonomer," 2009,Composite Interfaces, vol. 16, Nos. 7-9, pp. 923-935.
Chang et al., "Interactions of a Cationic Antimicrobial (ε-Polylysine) with an Anionic Biopolymer (Pectin): An Isothermal Titration Calorimetry, Microelectrophoresis, and Turbidity Study," J. Agric. Food Chem., 2011, 59 (10), pp. 5579-5588. (Abstract Only).
Chung, D., et al., "Release of Propyl Paraben from a Polymer Coating into Water and Food Simulating Solvents for Antimicrobial Packaging Applications," Apr. 2001, Journal of Food Processing and Preservation, vol. 25, Issue 1, pp. 71-87. (Abstract Only).
Gemili, S., "Preparation and Characterization of Antimicrobial Polymeric Films for Food Packaging Applications," Jul. 2007, Thesis, Izmir Institute of Technology, 83 pages.
Gowrisankar et al., "A General and Efficient Catalyst for Palladium-Catalyzed C-O Coupling Reactions of Aryl Halides with Primary Alcohols," Journal of the American Chemical Society, 2010, vol. 132, Issue 33, pp. 11592-11598.

(Continued)

Primary Examiner — Ali Soroush
Assistant Examiner — Yanzhi Zhang
(74) Attorney, Agent, or Firm — Foley & Lardner LLP

(57) ABSTRACT

A lignin derivative including one or more polycations is provided and an article including such a lignin derivative is also provided. Methods of inhibiting microbial growth with an article including such a lignin derivative are further provided.

22 Claims, No Drawings

(56) References Cited

OTHER PUBLICATIONS

Han, H.J., "Antimicrobial Food Packaging," Mar. 2000, Food Technology, vol. 54, No. 3, pp. 56-65.
Helander et al., Permeabilizing action of polyethyleneimine on *Salmonella typhimurium* involves disruption of the outer membrane and interactions with lipopolysaccharide, Microbiology, 1998, vol. 144, pp. 385-390.
International Search Report and Written Opinion for International Application No. PCT/US2012/044547, mail date Aug. 31, 2012, 9 pages.
International Search Report and Written Opinion for International Application No. PCT/US2012/027490, mail date Apr. 24, 2012, 13 pages.
Kenawy, El-Refaie, et al., "The Chemistry and APplications of Antimicrobial Polymers: A State-of-the-Art Review," May 2007, BioMacromolecules, vol. 8, No. 5, pp. 1359-1384.
La Storia, D. Antonietta, "Development and Application of Antimicrobial Food Production," 2008, Doctoral Thesis Research in Science and Technology of Agro-Food Production, University of Naples, Italy, 121 pages.
Layton, L., "FDA Says Studies on Triclosan, Used in Sanitizers and Soaps, Raise Concerns," Apr. 8, 2010, The Washington Post, Corrected Version, 2 pages.
Li, Y., et al., "Alkylated Kraft Lignin Based Thermoplastic Blends with Aliphatic Polyesters," 2002, ACS Publication, Macromolecules, Macromolecules, vol. 35, No. 26., pp. 9707-9715.
Li, Yan, "Final Report: Biodegradable Thermoplastic Natural Fiber Composite," 2007, Environmental Protection Agency, Extramural Research Project, 2 pages.
Liz Earle, Naturally Active Skincare, "Ingredients Factsheet: The Truth About Preservatives," 2012, Liz Earle Beauty Co. Limited, 3 pages.
National Committee for Clinical Laboratory Standards, "Methods for dilution antimicrobial susceptibility tests for bacteria that grow aerobically," 1993, National Committee for Clinical Laboratory Standards, Villanova, Pa.,3rd ed., vol. 13, No. 5, NCCLS Document M7-A3, 54 pages.
Sergeev et al., Selective, Nickel-Catalyzed Hydrogenolysis of Aryl Ethers, Science, 2011, vol. 332, pp. 439-443.
Smolander, M., "Potential Nanotechnology Applications in Food Packaging," Sep. 23-25, 2009, International Forum on Emerging Technologies in Food Processing, University of Illinois, Urbana, IL, USA, 29 pages.
Tecnaro GmbH, Definition of Arboform, retrieved from http://www.tecnaro.de/english/arboform.htm on Dec. 9, 2010, 1 page.
Tyler, C. I., "Types of Antimicrobial Packaging Systems," retrieved from http://www.ehow.com/print/list_6558172_types-antimicrobial-packaging-systems.html on Dec. 28, 2012, 2 pages.
Vaara, M., Agents that increase the permeability of the outer membrane, Microbiological Reviews, 1992, vol. 56, pp. 395-411.
Veluri et al., "Phytotoxic and Antimicrobial Activities of Catechin Derivatives," Journal of Agricultural and Food Chemistry, Dec. 15, 2004, vol. 52, Issue 25, p. 7746. (Entire article attached for reference).
Wilde, K.N., et al. "Evaluating the Cytotoxicity of Conjugated Polyelectrolyte Biocides," 2010, Abstract of Presentation at the American Institute of Chemical Engineers Annual Meeting, 1 page.
Smith, et al., "March's Advanced Organic Chemistry—Reactions, Mechanisms and Structure," 3rd Edition (1985), pp. 901-903.

\* cited by examiner

.US 9,095,142 B2

LIGNIN DERIVATIVES HAVING POLYCATIONS AND USES THEREOF

CROSS-REFERENCE TO RELATED APPLICATIONS

This application is a U.S. National Phase application of International Application No. PCT/US2012/044547, filed on Jun. 28, 2012, which is incorporated herein by reference in its entirety for any and all purposes.

FIELD

The present technology relates to a lignin derivative including one or more polycations and articles including such a lignin derivative. Also provided are methods of inhibiting microbial growth with an article including such a lignin derivative.

BACKGROUND

The following description is provided to assist the understanding of the reader. None of the information provided or references cited is admitted to be prior art to the present technology.

Native lignin is a naturally occurring, cross-linked, amorphous biopolymer that is an integral component of plant biomass. Lignin is the second most abundant biopolymer earth after cellulose, and contributes to the strength and rigidity of plants and trees. Lignin hinders the process of converting wood into paper because most of the lignin must first be removed from wood to liberate wood fibers for the production of paper. Consequently, the pulp and paper industry annually generates over 45 million metric tons of lignin as a by-product of chemically-processed wood pulps and over 10 million metric tons of lignin as a by-product of mechanically-processed wood pulps. Some of the by-product lignin is used to make short-life paper products such as newsprint and telephone directories, but the majority is being used internally by pulp producers as a low-grade fuel for the chemical pulping operation. Accordingly, there is significant economic incentive to find new markets and more valuable uses for by-product lignin.

SUMMARY

In accordance with one aspect, a lignin derivative is provided, where the lignin derivative includes one or more polycations. In some embodiments, the lignin derivative is an antimicrobial agent. For example, fit some embodiments, the lignin derivative is represented by Formula I:

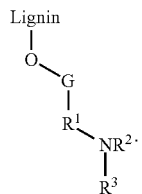

In Formula I, G is absent or a polymeric group; $R^1$ is a bond, alkylene, (alkyleneamino)$_q$, (alkyleneoxy)$_q$, (alkyleneoxyarylene)$_q$, or (alkyleneoxyarylene)alkylene (aryleneoxyalkylene)$_q$ wherein q is an integer of 1 to 10; $R^2$ is H or alkyl; and $R^3$ is a polycation. In some embodiments, $R^3$ is a polypeptide having at least one or more amino acid residues selected from lysine, histidine, arginine, tryptophan, ornithine, 2,4-diaminobutyric acid, 2,3-diamino, and combinations thereof, where at least one basic residue of the polypeptide is protonated. In other embodiments. $R^3$ is selected from poly(methylene-co-guanidine), poly-L-lysine, ε-poly-L-lysine, poly-L-ornithine, poly-L-arginine, poly-L-histidine, poly-L-tryptophan, poly-2,4-diaminobutyric acid, poly-2,3-diaminopropionic acid, and a protamine. In still other embodiments, $R^3$ is poly(methylene-co-guanidine) or ε-poly-L-lysine.

In accordance with another aspect, an article is provided, where the article includes any of the lignin derivatives described herein. In some embodiments, the article has antimicrobial activity.

In accordance with yet another aspect, a method is provided of inhibiting microbial growth, where the method includes contacting one or more microbes with any of lignin derivatives or articles described herein.

In accordance with an additional aspect, a method is provided for preparing a lignin derivative, where the method includes contacting a lignin-containing material with one or more groups of Formula II or IIA:

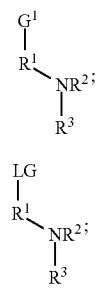

to form the lignin derivative, where the lignin derivative is represented by Formula I:

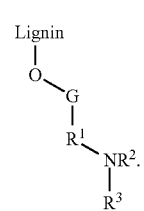

In Formula I and Formula II, $G^1$ is absent or a polymerizable group; G is absent or a polymeric group; LG is a leaving group; $R^1$ is a bond, alkylene, (alkyleneamino)$_q$, (alkyleneoxy)$_q$, (alkyleneoxyarylene)$_q$, or (alkyleneoxyarylene) alkylene(aryleneoxyalkylene)$_q$ where q is an integer of 1 to 10; $R^2$ is H or alkyl; and $R^3$ is a polycation.

The foregoing summary is illustrative only and is not intended to be in any way limiting. In addition to the illustrative aspects, embodiments and features described above, further aspects, embodiments and features will become apparent by reference to the detailed description.

DETAILED DESCRIPTION

The illustrative embodiments described in the detailed description and claims are not meant to be limiting. Other embodiments may be utilized, and other changes may be made, without departing from the spirit or scope of the subject matter presented here.

The present technology is described herein using several definitions, as set forth throughout the specification.

As used herein, unless otherwise stated, the singular forms "a," "an," and "the" include plural reference. Thus, for example, a reference to "an article" includes a plurality of articles, and a reference to "a compound" is a reference to one or more compounds.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Alkyl groups include straight chain, branched chain, or cyclic alkyl groups having 1 to 24 carbons or the number of carbons indicated herein. In some embodiments, an alkyl group has from 1 to 16 carbon atoms, from 1 to 12 carbons, from 1 to 8 carbons or, in some embodiments, from 1 to 6, or 1, 2, 3, 4 or 5 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. In some embodiments, the alkyl groups may be substituted alkyl groups. In some embodiments, the alkyl groups may be cycloalkyl groups.

Cycloalkyl groups are cyclic alkyl groups having from 3 to 10 carbon atoms. In some embodiments, the cycloalkyl group has 3 to 7 ring members, whereas in other embodiments the number of ring carbon atoms range from 3 to 5, 3 to 6, or 5, 6 or 7. Cycloalkyl groups further include monocyclic, bicyclic and polycyclic ring systems. Monocyclic groups include, e.g., cyclopropyl, cyclobutyl, cyclopentyl, cyclohexyl, and cycloheptyl groups. Bicyclic and polycyclic cycloalkyl groups include bridged or fused rings, such as, but not limited to, bicyclo[3.2.1]octane, decalinyl, and the like. Cycloalkyl groups include rings that are substituted with straight or branched chain alkyl groups as defined above. In some embodiments, the cycloalkyl groups are substituted cycloalkyl groups. Representative substituted alkenyl groups may be mono-substituted or substituted more than once, such as, but not limited to, mono-, di- or tri-substituted with substituents such as those listed above. Representative substituted alkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Thus, alkenyl groups have from 2 to 24 carbon atoms, and typically from 2 to 10 carbons or, in some embodiments, from 2 to 8, 2 to 6, or 2 to 4 carbon atoms. Examples include, but are not limited to vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, among others. Representative substituted alkenyl groups may be mono-substituted or substituted more than once, such as, but not limited to, mono-, di- or tri-substituted with substituents such as those listed above.

Aryl groups are cyclic aromatic hydrocarbons that do not contain heteroatoms. Thus aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, and naphthenyl groups. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once, such as, but not limited to, 2-, 3-, 4-, 5-, or 6-substituted phenyl or naphthyl groups, which may be substituted with groups including, but not limited to, amino, alkoxy, alkyl, cyano, and/or halo. In some embodiments, aryl is phenyl or naphthyl. In certain embodiments, aryl is phenyl.

Heteroaryl groups include an aromatic ring containing, for example, 5 to 12, or 5 to 10 atoms including one or more heteroatoms (e.g., 1, 2, 3 or 4 heteroatoms) selected from N, O and S and with the remaining ring atoms being carbon. Heteroaryl groups do not contain adjacent S and O atoms. Unless otherwise indicated, heteroaryl groups may be bound to the parent structure by a carbon or nitrogen atom, as valency permits. For example, "pyridyl" includes 2-pyridyl, 3-pyridyl and 4-pyridyl groups, and "pyrrolyl" includes 1-pyrrolyl, 2-pyrrolyl and 3-pyrrolyl groups. Heteroaryl groups may be monocyclic or polycyclic (e.g., bicyclic, tricyclic). In some embodiments, a heteroaryl group is monocyclic. Examples include pyrrole, pyrazole, imidazole, triazole (e.g., 1,2,3-triazole, 1,2,4-triazole, 1,2,4-triazole), tetrazole, furan, isoxazole, oxazole, oxadiazole, 1,2,3-oxadiazole, 1,2,4-oxadiazole, 1,3,4-oxadiazole), thiophene, isothiazole, thiazole, thiadiazole (e.g., 1,2,3-thiadiazole, 1,2,4-thiadiazole, 1,3,4-thiadiazole), pyridine, pyridazine, pyrimidine, pyrazine, triazine (e.g., 1,2,4-triazine, 1,3,5-triazine) and tetrazine. In some embodiments, more than one ring of a polycyclic heteroaryl group are aromatic. Examples include indole, isoindole, indazole, benzoimidazole, benzotriazole, benzofuran, and benzoxazole.

The terms "alkylene," "alkenylene," or "arylene," alone or as part of another substituent, means a divalent radical derived from an alkyl, cycloalkyl, alkenyl, aryl, or heteroaryl group, respectively, as exemplified by —CH$_2$CH$_2$CH$_2$CH$_2$—. For alkylene, alkenyl, or an linking groups, no orientation of the linking group is implied. Alkyleneamino is a divalent radical including alkylene and amino groups as defined herein. Alkyleneoxy is a divalent radical including alkylene and oxo groups as defined herein. Alkyleneoxyarylene and aryleneoxyalkylene are divalent radicals including alkylene, oxo, and aryl groups as defined herein.

The term "amine" (or "amino") as used herein refers to —NHR and —NRR' groups, where R, and R' are independently hydrogen, or a substituted or unsubstituted alkyl, alkenyl, alkynyl, cycloalkyl, aryl or aralkyl group as defined herein. Examples of amino groups include —NH$_2$, methylamino, dimethylamino, ethylamino, diethylamino, propylamino, isopropylamino, phenylamino, benzylamino, and the like.

The term "oxo" refers to a divalent oxygen group. While the term includes doubly bonded oxygen, such as that found in a carbonyl group, as used herein, the term oxo explicitly includes singly bonded oxygen of the form —O— which is part of a polymer backbone. Thus, an oxo group may be part of an ether linkage (—O—), an ester linkage (—O—C(O)—), a carbonate linkage (—O—C(O)O—), a carbamate linkage (O—C(O)NH— or —O—C(O)NR—), and the like.

"Substituted" refers to a chemical group as described herein that further includes one or more substituents, such as lower alkyl (including substituted lower alkyl such as hydroxyalkyl, aminoalkyl), aryl (including substituted aryl), acyl, halogen, hydroxy, amino, alkoxy, alkylamino, acylamino, thioamido, acyloxy, aryloxy, aryloxyalkyl, carboxy, thiol, sulfide, sulfonyl, oxo, both saturated and unsaturated cyclic hydrocarbons (e.g., cycloalkyl, cycloalkenyl)cycloheteroalkyls and the like. These groups may be attached to any carbon or substituent of the alkyl, alkenyl, alkynyl, aryl, cycloheteroalkyl, alkylene, alkenylene, alkynylene, arylene, hetero moieties. Additionally, the substituents may be pendent from, or integral to, the carbon chain itself.

The term "leaving group" or "LG" as used herein, is well known among those of skill in the art as a labile substituent of a compound that is readily displaced from the compound. Leaving groups, as used herein, are described in *March's Advanced Organic Chemistry*, (John Wiley, and Sons, 5$^{th}$ Edition, 2001), and encompass the group consisting of a halo or O(SO$_2$)R$^A$; where each R$^A$ is, independently, alkyl or aryl. In certain embodiments, each leaving group is, independently, a chloro; bromo; iodo;

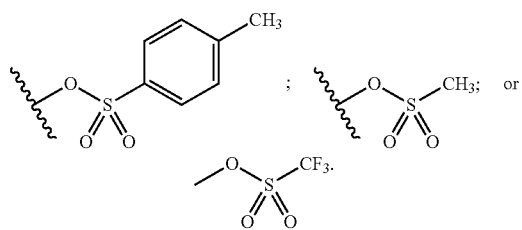

The term "moldable thermoplastic material," as used herein, refers to thermoplastic polymers known in the art, including polymers including at least one of a polyacrylate, a polymethacrylate, a polyolefin, a polyepoxy, a polyurethane, or a polyurea.

The term "polycation," as used herein, refers to a polycationic polymer, wherein at least 50% of the monomers within the polycationic polymer have at least one substituent that is configured to provide a positively charged amino substituent when protonated. The substituent may be an amino group. For example, the polycationic polymer may be a polycationic polypeptide. In some embodiments, at least 50% of the (natural or non-natural) amino acid residues within a polycationic polypeptide are basic amino acids, such as lysine ornithine, 2,3-diaminopropionic acid, or a combination thereof. The term "polycation," further encompasses the following compounds:

a) Protamines: Protamines are small (MW up to about 8000) strongly basic proteins, the positively charged amino acid groups of which (especially arginines) are usually arranged in groups. Protamines may be of natural origin or produced by recombinant methods.

b) Histones: Histones are small DNA-binding proteins present in the chromatin, having a high proportion of positively charged amino acids (lysine and arginine) which enable them to bind to DNA independently of the nucleotide sequence and fold it into nucleosomes.

c) Synthetic polypeptides: Synthetic polypeptides include homologous polypeptides (poly-lysine, poly-arginine) or heterologous polypeptides (consisting of two or more representatives of positively charged amino acids). Synthetic polypeptides further include non-natural amino acids such as 2,4-diaminobutyric acid and 2,3-diaminopropionic acid, etc.

d) Non-peptide polycations: Non-peptide polycations include aminoalkyl polymers such as a polyethyleneimine or spermine. Non-peptide polycations generally include from about 5 to 500 positively charged cations.

In some embodiments, the polycation includes lysine, histidine, arginine, tryptophan, ornithine, 2,4-diaminobutyric acid, 2,3-diaminopropionic acid, or a combination thereof. In some embodiments, at least one basic residue of the polypeptide is protonated. In other embodiments, the polycation is poly(methylene-co-guanidine), poly-L-lysine, ε-poly-L-lysine, poly-L-ornithine, poly-L-arginine, poly-L-histidine, poly-L-tryptophan, poly-2,4-diaminobutyric acid, poly-2,3-diaminopropionic acid, a protamine, polymyxin B nonapeptide (PMBN). In some embodiments, the polycation includes one or more polyalkylamines (e.g., polyethyleneimine (PEI) or spermine).

The term "antimicrobial polycation," as used herein, refers to any polycation that kills or inhibits the growth of bacteria (i.e., Gram-positive and/or Gram negative) and/or fungi. As noted, illustrative antimicrobial polycations include poly(methylene-co-guanidine), poly-L-lysine, ε-poly-L-lysine, poly-L-ornithine, poly-L-arginine, poly-L-histidine, poly-L-tryptophan, poly-2,4-diaminobutyric acid, poly-2,3-diaminopropionic acid, or combinations thereof. In some embodiments, at least one basic residue of the polypeptide is protonated. See, for example, Vaara, M. *Microbiol Rev* (1992) 56, 395-411; and Helander, I. M., Latva-Kala, K. & Lounatmaa, K. *Microbiology* (1998) 144, 385-390.

As used herein, the term "lignin" refers to a phenolic biopolymer found in vascular plants that provides rigidity and strength to their cell walls. The lignin polymeric structure may include several phenylpropanoid building units interconnected by ether and carbon-to-carbon linkages. The phenylpropane units are not linked to each other in any systematic order. The phenylpropane units may be methoxylated to various degrees (e.g., trans-coniferyl alcohol and trans-sinapyl alcohol) or non-methoxylated (e.g., trans-p-coumaryl alcohol). Various combinations of these phenylpropane units are polymerized to form the lignin biopolymer.

Extracting lignin from lignocellulosic feedstocks (e.g., plant material) during pulping generally results in irregular lignin fragments. As it is difficult to elucidate and characterize lignin, it may be described in terms of the lignocellulosic plant material from which it was obtained, e.g., hardwood lignins, softwood lignins, and annual fibre lignins, and/or the methods by which it was recovered, e.g., Kraft lignin or organosolv lignin.

Lignin derivatives, and articles made from such lignin derivatives, can be made from lignin recovered during or after pulping of lignocellulosic feedstocks. The pulp may be from any suitable lignocellulosic feedstock including hardwoods, softwoods, annual fibers, and combinations thereof. For example, hardwood feedstocks for the present technology may be selected from acacia, aspen, beech, eucalyptus, maple, birch, gum, oak, poplar, and combinations/hybrids thereof. Illustrative softwood feedstocks which may be used herein include cedar; fir; pine; spruce; and combinations thereof. Representative annual fiber feedstocks include biomass derived from annual plants, plants which complete their growth in one growing season and therefore must be planted yearly. Examples of annual fibers include: flax, cereal straw (wheat, barley, oats), sugarcane bagasse, rice straw, corn stover, corn cobs, hemp, fruit pulp, alfa grass, switchgrass, and combinations/hybrids thereof. Lignin derivatives of the present technology can be derived from any feedstock, including those described above.

Lignin derivatives, and articles made from such lignin derivatives, can be made from lignin recovered by a variety of methods. For example, lignin may be obtained by solvent extraction of finely ground wood (milled-wood lignin) or by acidic dioxane extraction (acidolysis) of wood. Derivatives of lignin can be also isolated from biomass pre-treated using steam explosion, dilute acid hydrolysis, ammonia fiber expansion, or autohydrolysis methods. Derivatives of native lignin can be recovered after pulping of lignocellulosics including industrially operated Kraft pulping, soda pulping, and sulphite pulping. Alternatively, the "organosolv" pulping methods known to those of ordinary skill may be used to produce lignin. One organosolv method uses ethanol/solvent pulping (i.e., the Alcell process); a second organosolv method uses alkaline sulphite anthraquinone methanol pulping (i.e., the "ASAM" process); a third organosolv process uses methanol pulping followed by methanol, NaOH, and anthraquinone pulping (i.e., the "organocell" process); a fourth organosolv process uses acetic acid/hydrochloric acid or formic acid pulping (i.e., the "acetosolv" process). Lignin derivatives of the present technology can be recovered by any known method, including those described above. Lignin derivatives may be prepared by functionalizing lignin through one or more of its various chemically active substituents, such as hydroxyl groups.

In another aspect, an article containing depolymerized lignin is also provided. The lignin may be depolymerized either prior to being functionalized through one or more of its various chemically active substituents, or the lignin may be depolymerized after being functionalized.

Depolymerized lignin or lignin derivatives may be prepared, for example, by a process that includes either the hydrogenolysis of lignin or, alternatively, the acid-catalyzed or base-catalyzed treatment of lignin to produce smaller sized lignin particles having an average particle size ranging from, for example, about 40 nanometers (nm) to about 4,000 nm. Alternatively, depolymerized lignin may have an average particle size ranging from, for example, about 40 nm to about 1,000 nm, or from about 40 nm to about 500 nm. Such treated lignin may be referred to herein as "depolymerized lignin." As noted, depolymerizing lignin may include a hydrogenolysis reaction. The hydrogenolysis reaction may be catalyzed by a transition metal nickel, iron, copper, platinum, or palladium) catalyst. The transition metal catalyst will generally include one or more ligands, such as carbene ligands. Illustrative carbene ligands include N,N'-bis(2,6-diisopropylphenyl)-4,5-dihydroimidazol-2-ylidene (SIPr), bis(1,3-(2,4,6-trimethylphenyl)imidazol-2-ylidene) (IMes), (N,N'-bis(2,6-diisopropylphenyl)imidazol-2-ylidene) (IPr), N,N'-bis (adamantyl)imidazol-2-ylidene (IAd), 1,3-di-tert-butylimidazol-2-ylidene (ItBu), 1,3-dicyclohexyl-1,3-dihydro-2H-imidazol-2-ylidene (ICy), and 1,3-diisopropyl-4,5-dimethylimidazol-2-ylidene (iPrIM).

Depolymerized lignin or lignin derivatives may also be obtained upon treatment of lignin with acid, such as for example, hydrochloric acid, sulfuric acid, and mixtures thereof, although other acid catalysts, including Lewis acid catalysts, could be used. Alternatively, depolymerized lignin may also be obtained upon treatment of the lignin material with a base, such as NaOH, KOH, Ca(OH)$_2$, Mg(OH)$_2$ and mixtures thereof, although other base catalysts could be used.

The depolymerization of lignin or lignin derivatives by a process that includes either the hydrogenolysis of lignin or, alternatively, the acid-catalyzed or base-catalyzed treatment of lignin may be conducted in the presence of a solvent. The dissolved lignin material can then be subjected to reaction conditions sufficient to at least partially depolymerize the lignin material. The solvents are chosen to achieve solvolysis of lignin, facilitate depolymerization of lignin, and inhibit repolymerization of lignin. Illustrative solvents may include methanol, ethanol, water, and dimethoxyethane, and dimethyl ether.

The instant technology is generally directed to a lignin derivative, where the lignin derivative includes a moiety derived from a polycation. Also provided are methods of inhibiting microbial growth with in article including such a lignin derivative having a polycation. The lignin derivatives having a polycation are characterized by providing protection to an article or materials containing the lignin derivatives from degradation by microbes including bacteria and fungi.

In one aspect, lignin derivatives are provided having a polycation. The polycation may be an antimicrobial polycation. For example, an antimicrobial polycation, such as poly (methylene-co-guanidine), poly-L-lysine, ε-poly-L-lysine, poly-L-ornithine, poly-L-arginine, poly-L-histidine, poly-L-tryptophan, poly-2,4-diaminobutyric acid, poly-2,3-diaminopropionic acid, or combinations thereof, where at least one basic residue of the polypeptide is protonated, can be covalently attached to lignin to impart antimicrobial activity to the lignin derivative. As noted, native lignin is a crosslinked amorphous organic biopolymer. The lignin derivatives of the present technology may optionally be depolymerized to various degrees. For example, the lignin derivatives of the present technology may be depolymerized before one or more antimicrobial polycations are attached to the depolymerized lignin. Alternatively, one or more antimicrobial polycations can be attached to lignin prior to depolymerization, because the antimicrobial activity of the lignin derivatives of the present technology persists even after depolymerization. In some embodiments, the lignin is covalently attached to the polycations. In some embodiments, the lignin is covalently attached to the polycations via a linker.

In some embodiments, the modified lignin derivative exhibits antimicrobial activity and thus can be incorporated into numerous articles. The articles may be for use in antimicrobial applications. In some embodiments, the article may an antimicrobial packaging, a food packaging, pharmaceutical, cosmetic, or perfume. In some embodiments, the lignin derivative and/or the article is a moldable thermoplastic material. In other embodiments, the article is a cloth, a garment, a coating, packaging, paper product (e.g., cardboard), drywall (i.e., plasterboard, wallboard, or gypsum board for construction), medical equipment or a toy.

In accordance with one aspect, a lignin derivative is provided, where the lignin derivative includes one or more polycations. In some embodiments, the lignin derivative is an antimicrobial agent. For example, in some embodiments, the lignin derivative is represented by Formula I:

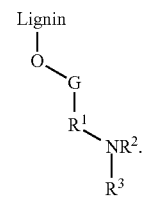

In Formula I, G is absent or a polymeric group; $R^1$ is a bond, alkylene, (alkyleneamino)$_q$, (alkyleneoxy)$_q$, (alkyleneoxyarylene)$_q$ or (alkyleneoxyarylene)alkylene(aryleneoxyalkylene)$_q$, wherein q is an integer of 1 to 10; $R^2$ is H or alkyl; and $R^3$ is a polycation.

In some embodiments, G includes a group selected from a polyacrylate, polyalkylacrylate, polymethacrylate, polyacrylamide, polyolefin, polyepoxide, polyurethane, and polyurea.

In other embodiments, G is absent. In some embodiments, Lignin-OGR¹— is a group of formula:

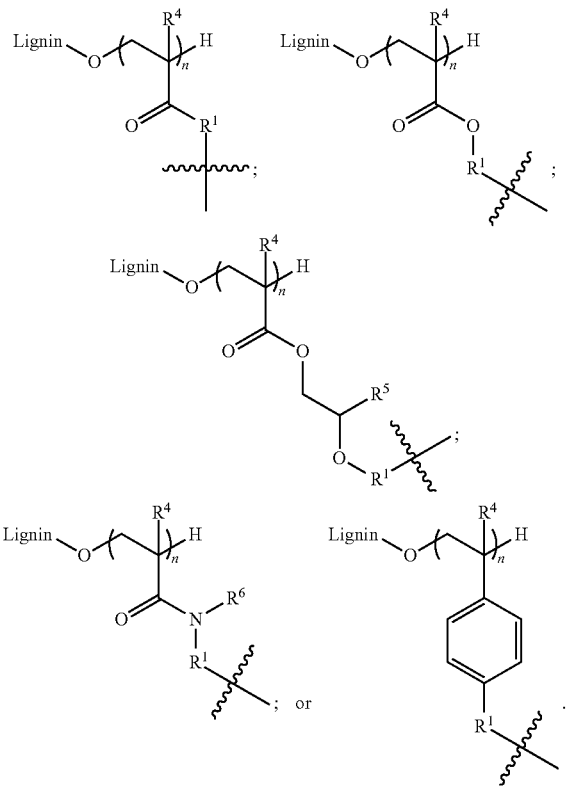

In the above formulae, R⁴ is H, alkyl, alkenyl, alkynyl, alkoxy, ester, or CN; R⁵ is H or alkyl; R⁶ is H or alkyl; and n is an integer of 1 to 1000. In some embodiments, Lignin-OGR¹— is a group of formula:

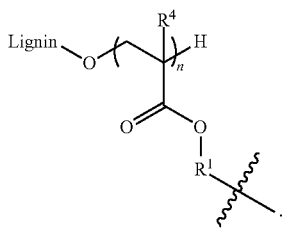

In other embodiments, R⁵, and R⁶ is each independently H or C₁-C₄ some embodiments, R¹ is an alkylene, (alkyleneoxy)$_q$, (alkyleneoxyarylene)$_q$ or (alkyleneoxyarylene)alkylene(aryleneoxyalkylene)$_q$ moiety. In other embodiments, R¹ is

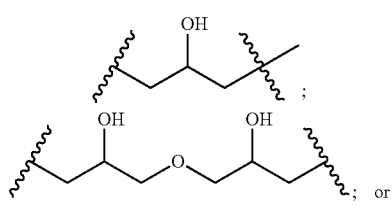

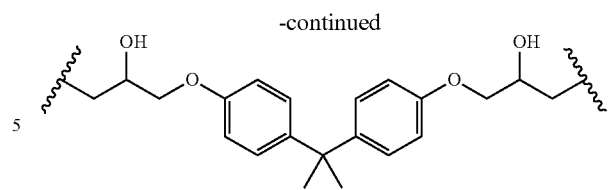

In other embodiments, R¹ is

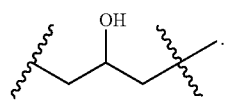 [SMILES: *CC(O)C*]

In some embodiments. R¹ is a bond and Lignin-OGR¹— is

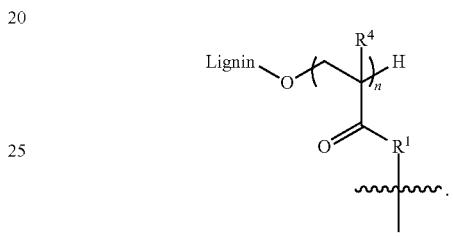

In other embodiments, R³ is a polypeptide having at least one or more amino acid residues selected from lysine, histidine, arginine, tryptophan, ornithine, 2,4-diaminobutyric acid, 2,3-diaminopropionic acid, and combinations thereof, where at least one basic residue of the polypeptide is protonated. In some embodiments, R³ is selected from poly(methylene-co-guanidine), poly-L-lysine, ε-poly-L-lysine, poly-L-ornithine, poly-L-arginine, poly-L-histidine, poly-L-tryptophan, poly-2,4-diaminobutyric acid, poly-2,3-diaminopropionic acid, and a protamine. In other embodiments, R³ is poly(methylene-co-guanidine) or ε-poly-L-lysine.

According to another aspect, an article including a lignin derivative is provided, where the lignin derivative includes one or more polycations, in some embodiments, the article is an antimicrobial agent. For example, in some embodiments, the lignin derivative is represented by Formula I:

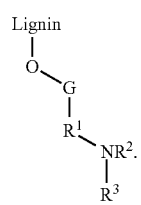

I

In Formula I, G is absent or a polymeric group; R¹ is a bond, alkylene, (alkyleneamino)$_q$, (alkyleneoxy)$_q$, (alkyleneoxyarylene)$_q$ or (alkyleneoxyarylene)alkylene(aryleneoxyalkylene)$_q$ moiety, wherein q is an integer of 1 to 10; R² is H or alkyl; and R³ is a polycation. In some embodiments, the article is an antimicrobial agent. In some embodiments, the lignin derivative is as described anywhere herein.

According to another aspect, a method is provided of inhibiting microbial growth, where the method includes contacting one or more microbes with any of the lignin derivatives or articles described herein. The one or more microbes may include, but are not limited to, bacteria or fungi. For example, the bacteria may include Gram-positive and/or Gram negative bacteria. In some embodiments, the method includes contacting one or more microbes with an article including a lignin derivative, where the lignin derivative is represented by Formula I:

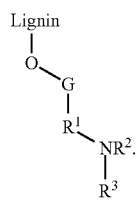

I

In Formula $G^1$ is absent or a polymerizable group; G is absent or a polymeric group; $R^1$ is a bond, alkylene, (alkyleneoxy)$_q$, (alkyleneamino)$_q$, (alkyleneoxyarylene)$_q$ or (alkyleneoxyarylene)alkylene(aryleneoxyalkylene)$_q$ moiety; $R^2$ is or alkyl; and $R^3$ is a polycation. The one or more microbes may include, but are not limited to, bacteria or fungi. For example, the bacteria may include Gram-positive or Gram-negative bacteria.

The antimicrobial activity of the lignin derivatives, or articles thereof, can be evaluated according to various methods, such as those described in the American Association of Textile and Color Chemists (AATCC) Test Method 100-1993, as published in the AATCC Technical Manual, 1997, pages 143-144, and as described in published U.S. patent application No. 2011/0117176. Samples of the articles including any of the lignin derivatives having antimicrobial moieties may be evaluated according to Test Method 100-1993 for percent reductions in, for example, *Staphylococcus aureus* colony forming units (CFU) after, for example, a 24-hour exposure time at temperatures of about 25° C.

Alternatively, the antimicrobial activity of lignin derivatives, or articles including the lignin derivatives, can be evaluated according to high throughput methods, such as those described by the National Committee for Clinical Laboratory Standards (NCCLS), Villanova, Pa., *Approved standard M7-A3: Methods for dilution antimicrobial susceptibility tests for bacteria that grow aerobically*, (1993) 3$^{rd}$ ed, and as described in published U.S. patent application No. 2010/0240592. For example, the antimicrobial activities of lignin derivatives of the present technology, or articles thereof, may be determined in 96-well plates Nunclon® polystyrene) by the standard NCCLS broth microdilution method. Illustrative microorganisms that may be used to determine antibiotic activity include *Escherichia coli* (ATCC 25922) or *Pseudomonas aeruginosa* (*P. aeruginosa* ATCC 27853). Antimicrobial activities may be expressed as the minimal inhibitory concentration (MIC) in µg/ml at which no visible growth observed after, for example, 18-20 hours of incubation at, for example, 37° C.

According to another aspect, a method is provided for preparing a lignin derivative, where the method includes contacting a lignin-containing material with one or more groups of Formula II or IIA:

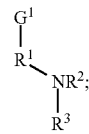

II

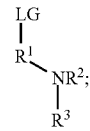

IIA to form the lignin derivative, where the lignin derivative is represented by Formula I:

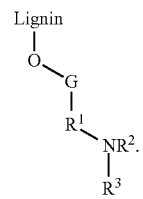

I

In Formula I, II, and IIA $G^1$ is absent or a polymerizable group; G is absent or a polymeric group; $R^1$ is a bond, alkylene, (alkyleneamino)$_q$, (alkyleneoxy)$_q$, (alkyleneoxyarylene)$_q$ or (alkyleneoxyarylene)alkylene(aryleneoxyalkylene)$_q$ moiety, where q is an integer of 1 to 10; $R^2$ is H alkyl; $R^3$ is a polycation, and LG is a leaving group.

In some embodiments, $G^1$ and G are absent. In other embodiments, $G^1$ is a group of formula:

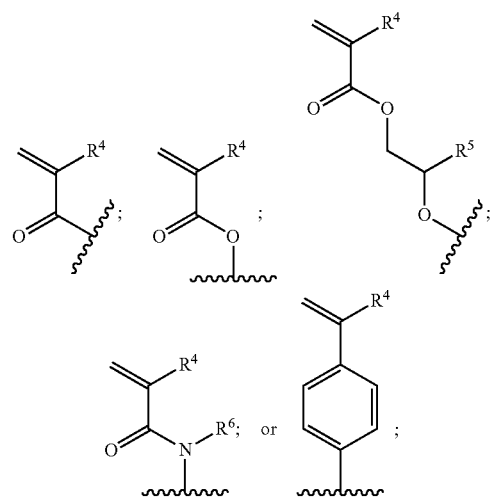

and Lignin-OGR$^1$— is a group of formula:

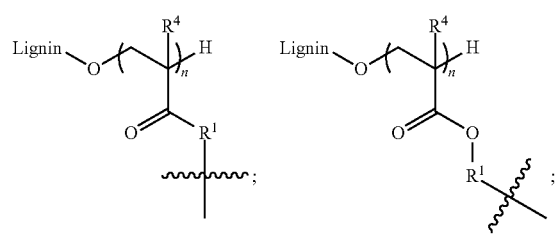

-continued

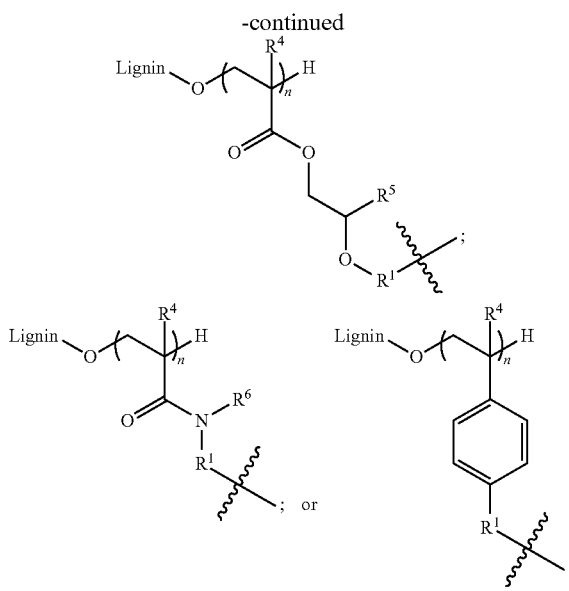

In the above formulae, R⁴ is H, alkyl, alkenyl, alkynyl, alkoxy, ester, or CN; R⁵ is H or alkyl; R⁶ is H or alkyl; and n is an integer of 1 to 1000.

In other embodiments, G¹ is a group of formula:

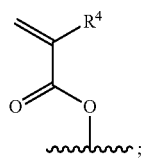

and Lignin-OGR¹— is a group of formula:

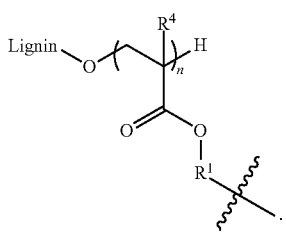

In some embodiments, R², R⁴, R⁵ and R⁶ is each independently H or $C_1$-$C_4$ alkyl.

In other embodiments, R¹ is an alkylene, (alkyleneoxy)$_q$, (alkyleneoxyarylene)$_q$ or (alkyleneoxyarylene)alkylene (aryleneoxyalkylene)$_q$ moiety. In some embodiments, R¹ is

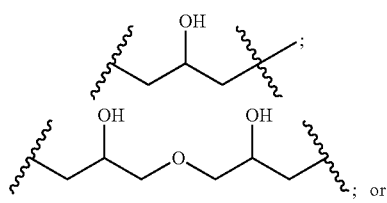

-continued

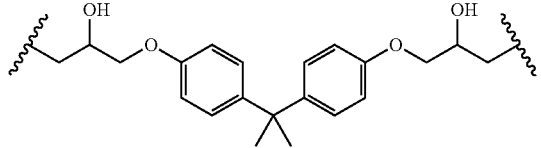

In other embodiments, R¹ is

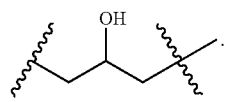

In some embodiments, R¹ is a bond; G¹ is

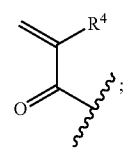

and Lignin-OGR¹— is

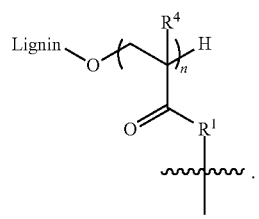

In other embodiments, R³ is a polypeptide having at least one or more amino acid residue selected from lysine, histidine, arginine, tryptophan, ornithine, 2,4-diaminobutyric acid, 2,3-diaminopropionic acid, and combinations thereof, where at least one basic residue of the polypeptide is protonated. In some embodiments, R³ is selected from poly(methylene-co-guanidine), poly-L-lysine, ε-poly-L-lysine, poly-L-ornithine, poly-L-arginine, poly-L-histidine, poly-L-tryptophan, poly-2,4-diaminobutyric acid, poly-2,3-diaminopropionic acid, and a protamine. In other embodiments, R³ is poly(methylene-co-guanidine) or ε-poly-L-lysine.

In some embodiments, LG is chloro; bromo; iodo;

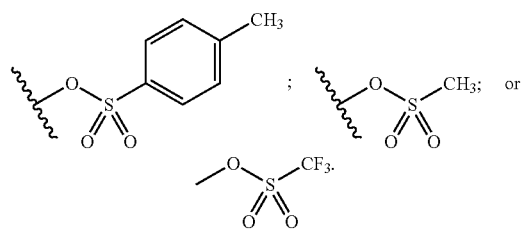

In some embodiments, the contacting step may also include a polymerizing step. The polymerizing step may also include activating the polymerizable group. For example, activation of the polymerizable group may include heating the polymerizable group, applying ultraviolet irradiation to the polymerizable group, adding a thermal initiator to the polymerizable group, adding a photochemical initiator to the polymerizable group, adding an oxidant to the polymerizable group, or adding a combination thereof. Where the activating the polymerizable group includes adding a thermal initiator to the polymerizable group, the thermal initiator may include, but is not limited to, an azonitrile, acyl peroxide, azobisisobutyronitrile, ammonium persulfate, 4,4-azobis(4-cyanovaleric acid), 1,1'-azobis(cyclohexanecarbonitrile), 2,2'-azobisisobutyronitrile, benzoyl peroxide, tert-butyl peracetate, lauroyl peroxide, or dicumyl peroxide. Where the activating the polymerizable group includes adding a photochemical initiator to the polymerizable group, the initiator may include, but is not limited to, 3-butyl-2-[5-(1-butyl-3,3-di methyl-1,3-dihydro-indol-2-ylidene)-penta-1,3-dienyl]-1,1-dimethyl-1H-benzo[e]indolium triphenylbutylborate, 3-butyl-2-[5-(3-butyl-1,1-dimethyl-1,3-dihydro-benzo[e]indol-2-ylidene)-penta-1,3-dienyl]-1,1-dimethyl-1,1-benzo[e]indolium triphenylbutylborate, 6-hydroxy-2,4,5,7-tetraiodo-3-oxo-9,9a-dihydro-3H-xanthene-9-carbonitrile, 2,2-dimethoxy-2-phenylacetophenone, 2-hydroxy-2-methylpropiophenone, or 9,10-phenanthrenequinone. Where the activating the polymerizable group includes adding an oxidant to the polymerizable group, the initiator may include, but is not limited to, eerie ammonium nitrate (CAN). In some embodiments, the step of activating the polymerizable group includes heating the polymerizable group to a temperature of about 40° C. to about 120° C.

Depending on the application, the method of modifying lignin with one or more antimicrobial polycations to form a lignin derivative may further include at least partially depolymerizing the lignin before forming the lignin derivative. Alternatively, the at least partially depolymerizing the lignin derivative may occur after formation of the lignin derivative. In some embodiments, the depolymerizing includes treating the lignin or the lignin derivative with an acid catalyst. In other embodiments, the depolymerizing includes treating the lignin or the lignin derivative with a basic catalyst. In some embodiments, the depolymerizing includes subjecting the lignin or the lignin derivative to a hydrogenolysis reaction. In other embodiments, the hydrogenolysis reaction is conducted in the presence of a transition metal catalyst. In some embodiments, the transition metal catalyst includes nickel. In other embodiments, the transition metal catalyst further includes a carbene ligand. In some embodiments, the carbene ligand is selected from the group consisting of N,N'-bis(2,6-diisopropylphenyl)-4,5-dihydroimidazol-2-ylidene (SIPr), bis(1,3-(2,4,6-trimethylphenyl)imidazol-2-ylidene) (IMes), (N,N'-bis(2,6-diisopropylphenyl)imidazol-2-ylidene) (IPr), N,N'-bis(adamantyl)imidazol-2-ylidene (IAd), 1,3-di-tert-butylimidazol-2-ylidene (ItBu), 1,3-dicyclohexyl-1,3-dihydro-2,1-imidazol-2-ylidene (ICy), and 1,3-diisopropyl-4,5-dimethylimidazol-2-ylidene (iPrIM). In other embodiments, the carbene ligand is N,N'-bis(2,6-diisopropylphenyl)-4,5-dihydroimidazol-2-ylidene (SIPr). In one embodiment, the carbene ligand is N,N'-bis(2,6-diisopropylphenyl)-4,5-dihydroimidazol-2-ylidene (SIPr).

According to another aspect, a method is provided for coating an article with a lignin derivative, where the method includes contacting an article with one or more groups of Formula I:

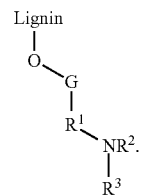

I

In Formula I, $G^1$ is absent or a polymerizable group; G is absent or a polymeric group; $R^1$ is a bond, alkylene, (alkyleneoxy)$_q$, (alkyleneamino)$_q$, (alkyleneoxyarylene)$_q$ or (alkyleneoxyarylene)alkylene(aryleneoxyalkylene)$_q$ moiety; $R^2$ is H or alkyl; and $R^3$ is a polycation.

In some embodiments, the article may an antimicrobial packaging, a food packaging, pharmaceutical, cosmetic, or perfume. In some embodiments, the article is a moldable thermoplastic material. In other embodiments, the article is a cloth, a garment, a coating, packaging, paper product (e.g., cardboard), drywall (i.e., plasterboard, wallboard, or gypsum board for construction), medical equipment or a toy.

The present technology, thus generally described, will be understood more readily by reference to the following Examples, which are provided by way of illustration and are not intended to be limiting of the present technology.

EXAMPLES

It will be appreciated that were reaction conditions (e.g., temperatures, times, mole ratios of reactants, solvents, pressures, etc.) are given, other conditions can also be used unless otherwise stated. Optimum reaction conditions may vary with the particular reactants or solvent used, but such conditions can be determined by one skilled in the art by routine optimization procedures.

Example 1

Synthesis of a Lignin Derivative Having Polycations

Lignin may be co-polymerized with a polycation such as poly-lysine as shown below in Scheme 1.

Step 1:

Poly-lysine is converted to a polymerizable intermediate by reacting the nucleophilic poly-lysine with an electrophilic polymerizable moiety-containing reagent, such as 2-hydroxypropyl acrylate, to provide a polymerizable poly-lysine intermediate. This first step can be conducted in the absence or presence of a solvent (e.g., tetrahydrofuran, dimethylformamide, etc.) and at a temperature of about 25° C. to about 60° C.

Step 2:

The polymerizable poly-lysine intermediate is then reacted with lignin and polymerized by combining the polymerizable poly-lysine intermediate with lignin in the presence of eerie ammonium nitrate (CAN). This step can be conducted in the absence or presence of a solvent (e.g., tetrahydrofuran, dimethylformamide, etc.) and at a temperature of about 25° C. to about 60° C.

Scheme 1

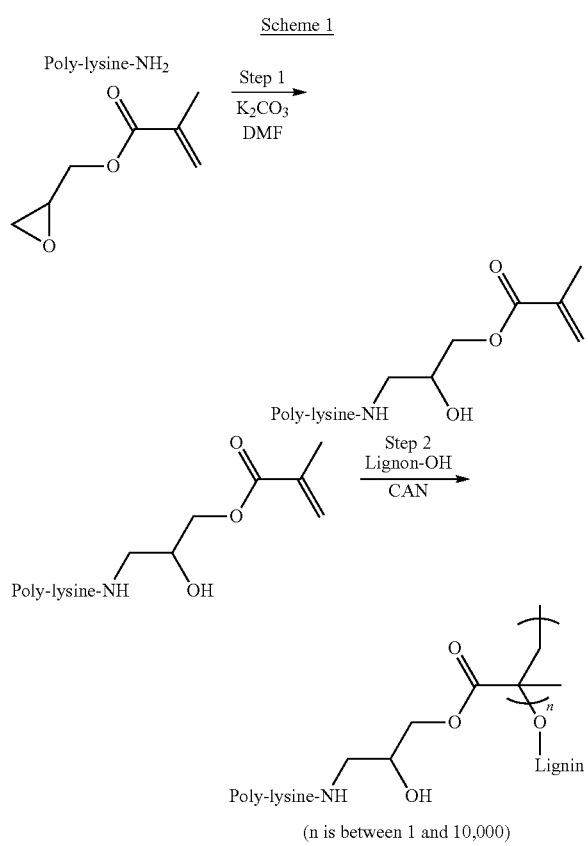

(n is between 1 and 10,000)

Example 2

Packaging Having Lignin Derivatives with Polycations

An article, such as polymer packaging, can be prepared, for example, by combining the lignin derivative having polycations of Example 1 with a polymer (e.g., polyester, polyolefin, or polyamide) to form a mixture, heating the mixture, and extruding the heated mixture to form the polymer packaging. Polyethylene pellets (0.95 kg) are combined with pellets of the lignin derivative having polycations of Example 1 (0.05 kg) and the resulting mixture is heated until it melts. The melted mixture is stirred and extruded into sheets (10 meters× 0.5 meters×1 millimeter), cooled, and the cooled sheets rolled. The resulting sheets of polymer packaging, which includes polyethylene and the lignin derivative having polycations, is expected to demonstrate improved antimicrobial activity relative to sheets of polymer packaging made only from polyethylene.

Example 3

Antimicrobial Testing Articles Having Lignin Derivatives with Polycations

The antimicrobial activity of the articles of this technology can be evaluated according to methods known to those of skill in the art, such as those described in U.S. patent publication No. 2011/0117176. For example, articles having lignin derivatives with polycations can be cut into square samples (e.g., about 3.0 cm by 3.0 cm) and evaluated for antimicrobial activity according to the American Association of Textile and Color Chemists (AATCC) Test Method 100-1993, as published in the AATCC Technical Manual, 1997, pages 143-144. The Test Method may include, for example, a suitable strain of *Staphylococcus aureus*, Tryptic Soy Broth as the nutrient broth, and/or Tryptic Soy Agar as the nutrient agar. Samples of the articles having lignin derivatives with polycations may then be evaluated for percent reductions in *S. aureus* colony forming units (CFU) after, for example, a 24-hour exposure time at temperatures of about 25° C. it is contemplated that the articles having lignin derivatives with polycations will have greater antimicrobial properties (e.g., percent reductions in *S. aureus* colony forming units) than corresponding articles that lack such lignin derivatives with polycations.

EQUIVALENTS

The embodiments, illustratively described herein may suitably be practiced in the absence of any element or elements, limitation or limitations, not specifically disclosed herein. Thus, for example, the terms 'comprising,' 'including,' 'containing,' etc. shall be read expansively and without limitation. Additionally, the terms and expressions employed herein have been used as terms of description and not of imitation, and there is no intention in the use of such terms and expressions of excluding any equivalents of the features shown and described or portions thereof, but it is recognized that various modifications are possible within the scope of the claimed technology. Additionally, the phrase 'consisting essentially of' will be understood to include those elements specifically recited and those additional elements that do not materially affect the basic and novel characteristics of the claimed technology. The phrase 'consisting of' excludes any element not specified.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent compositions, apparatuses, and methods within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as 'up to,' 'at least,' 'greater than,' 'less than,' and the like, include the number recited and refer to ranges which can be subsequently broken down into subranges as discussed above. Similarly, the phrase "at least about" some value such as, e.g., wt % includes at least the value and about the value. For example "at least about 1 wt %" means "at least 1 wt % or about 1 wt %." as will be understood by one skilled in the art, a range includes each individual member.

While certain embodiments have been illustrated and described, it should be understood that changes and modifications can be made therein in accordance with ordinary skill in the art without departing from the technology in its broader aspects as defined in the following claims.

What is claimed is:

1. A lignin derivative represented by the Formula I:

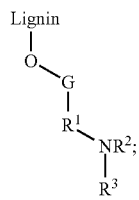

wherein:
G is absent or a polymeric group;
$R^1$ is an alkylene, (alkyleneamino)$_q$, (alkyleneoxy)$_q$, (alkyleneoxyarylene)$_q$, or (alkyleneoxyarylene)alkylene(aryleneoxyalkylene)$_q$ moiety, wherein q is from 1 to 10;
$R^2$ is H or alkyl;
$R^3$ is a polycation; and
the Lignin is a lignin product derived from a process comprising extraction of finely ground wood, acidic dioxane extraction of wood, steam explosion, dilute acid hydrolysis, ammonia fiber expansion of a biomass, pulping of lignocellulosics, hydrogenolysis of lignin, the acid-catalyzed or base-catalyzed treatment of lignin, or combination of two or more thereof.

2. The lignin derivative of claim 1, wherein the lignin derivative is thermoplastic.

3. The lignin derivative of claim 1, wherein G comprises a group selected from a polyacrylate, polyalkylacrylate, polymethacrylate, polyacrylamide, polyolefin, polyepoxide, polyurethane, and polyurea.

4. The lignin derivative of claim 1, wherein G is absent.

5. The lignin derivative of claim 1, wherein Lignin-OGR$^1$— is a group of formula:

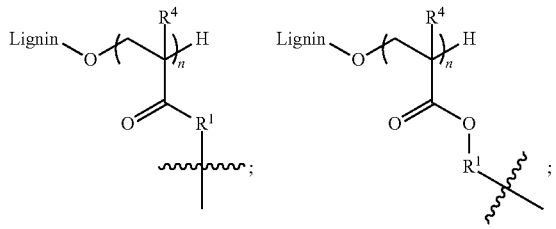

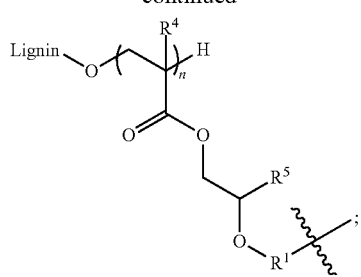

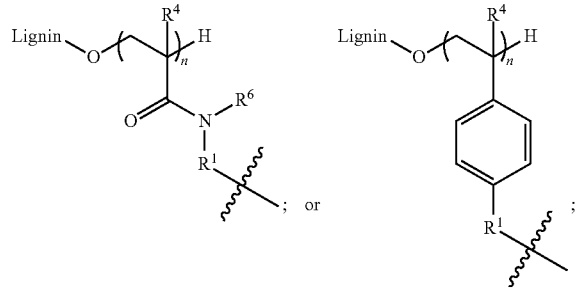

wherein:
$R^4$ is H, alkyl, alkenyl, alkynyl, alkoxy, ester, or CN;
$R^5$ is H or alkyl;
$R^6$ is H or alkyl; and
n is from 1 to 1000.

6. The lignin derivative of claim 5, wherein $R^2$, $R^4$, $R^5$, and $R^6$ is each independently H or $C_1$-$C_4$ alkyl.

7. The lignin derivative of claim 1, wherein $R^1$ is

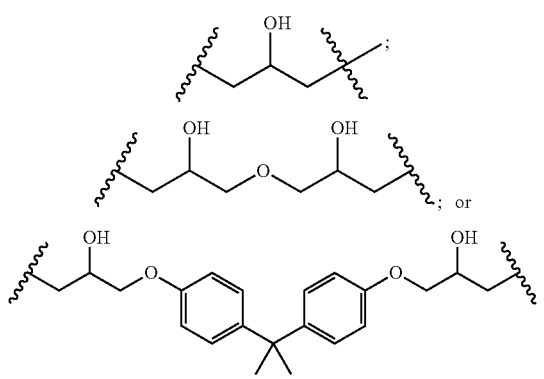

8. The lignin derivative of claim 1, wherein $R^3$ is a polypeptide having at least one or more amino acid residues selected from lysine, histidine, arginine, tryptophan, ornithine, 2,4-diaminobutyric acid, and 2,3-diaminopropionic acid, and wherein at least one basic residue of the polypeptide is protonated.

9. The lignin derivative of claim 1, wherein $R^3$ is selected from poly(methylene-co-guanidine), poly-L-lysine, ϵ-poly-L-lysine, poly-L-ornithine, poly-L-arginine, poly-L-histidine, poly-L-tryptophan, poly-2,4-diaminobutyric acid, poly-2,3-diaminopropionic acid, and a protamine.

10. The lignin derivative of claim 1, wherein $R^3$ is poly(methylene-co-guanidine) or s-poly-L-lysine.

11. An article comprising a lignin derivative represented by Formula I:

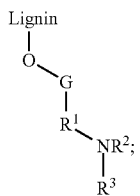

wherein:
G is absent or a polymeric group;
R$^1$ is an alkylene, (alkyleneamino)$_q$, (alkyleneoxy)$_q$, (alkyleneoxyarylene)$_q$, or (alkyleneoxyarylene)alkylene(aryleneoxyalkylene)$_q$ moiety, wherein q is from 1 to 10;
R$^2$ is H or alkyl;
R$^3$ is a polycation; and
the Lignin is a lignin product derived from a process comprising extraction of finely ground wood, acidic dioxane extraction of wood, steam explosion, dilute acid hydrolysis, ammonia fiber expansion of a biomass, pulping of lignocellulosics, hydrogenolysis of lignin, the acid-catalyzed or base-catalyzed treatment of lignin, or combination of two or more thereof;
wherein the article is a packaging, pharmaceutical, cosmetic, perfume, thermoplastic, garment, paper product, drywall, medical equipment, or toy.

12. The article of claim 11, wherein G is absent.

13. The article of claim 11, wherein Lignin-OGR$^1$— is a group of formula:

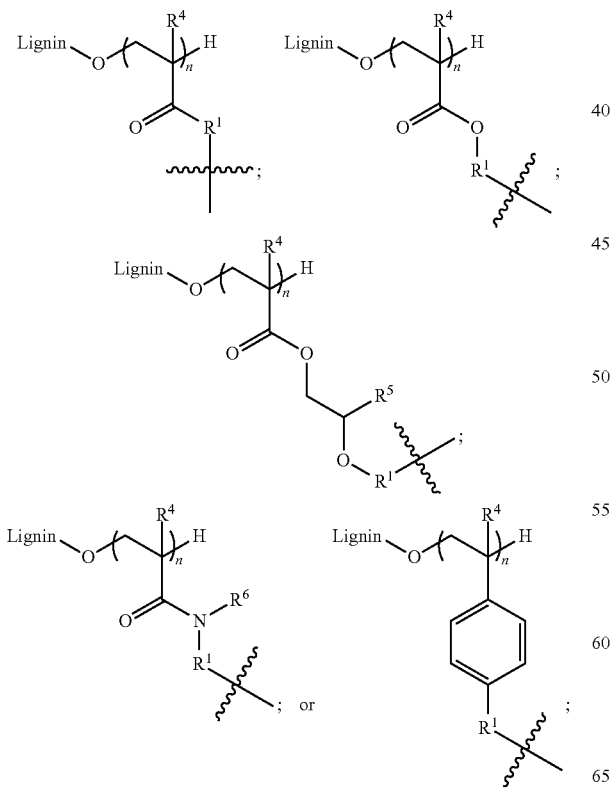

wherein:
R$^4$ is H, alkyl, alkenyl, alkynyl, alkoxy, ester, or CN;
R$^5$ is H or alkyl;
R$^6$ is H or alkyl;
n is from 1 to 1000; and
the Lignin is a lignin product derived from a process comprising extraction of finely ground wood, acidic dioxane extraction of wood, steam explosion, dilute acid hydrolysis, ammonia fiber expansion of a biomass, pulping of lignocellulosics, hydrogenolysis of lignin, the acid-catalyzed or base-catalyzed treatment of lignin, or combination of two or more thereof.

14. The article of claim 11, wherein G comprises a group selected from a polyacrylate, polyalkylacrylate, polymethacrylate, polyacrylamide, polyolefin, polyepoxide, polyurethane, and polyurea.

15. A method of inhibiting microbial growth, the method comprising: contacting one or more microbes with an article comprising a lignin derivative, wherein the lignin derivative is represented by Formula I:

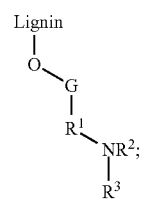

wherein:
G is absent or a polymeric group;
R$^1$ is an alkylene, (alkyleneamino)$_q$, (alkyleneoxy)$_q$, (alkyleneoxyarylene)$_q$, or (alkyleneoxyarylene)alkylene(aryleneoxyalkylene)$_q$ moiety, wherein q is from 1 to 10;
R$^2$ is H or alkyl;
R$^3$ is a polycation; and
the Lignin is a lignin product derived from a process comprising extraction of finely ground wood, acidic dioxane extraction of wood, steam explosion, dilute acid hydrolysis, ammonia fiber expansion of a biomass, pulping of lignocellulosics, hydrogenolysis of lignin, the acid-catalyzed or base-catalyzed treatment of lignin, or combination of two or more thereof.

16. The method of claim 15, wherein the one or more microbes comprise bacteria or fungi.

17. The method of claim 15, wherein G is absent.

18. The method of claim 15, wherein Lignin-OGR$^1$— is a group of formula:

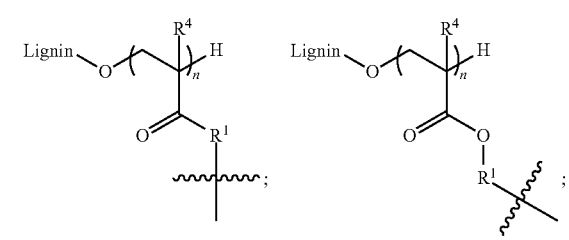

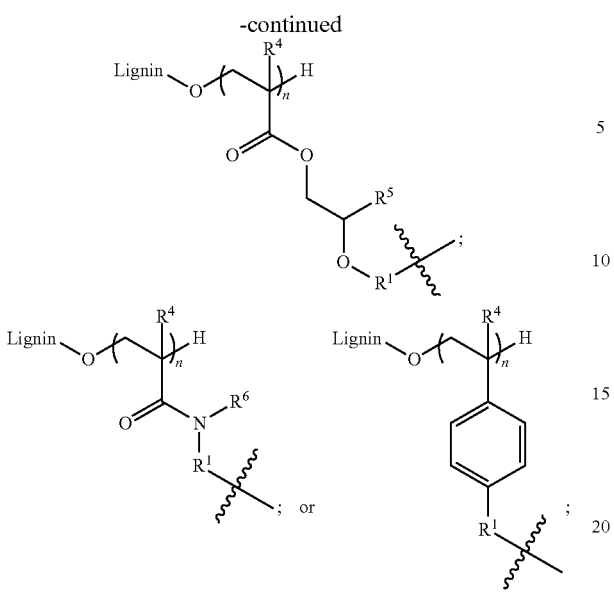

wherein:
R⁴ is H, alkyl, alkenyl, alkynyl, alkoxy, ester, or CN;
R⁵ is H or alkyl;
R⁶ is H or alkyl;
n is from 1 to 1000; and
the Lignin is a lignin product derived from a process comprising extraction of finely ground wood, acidic dioxane extraction of wood, steam explosion, dilute acid hydrolysis, ammonia fiber expansion, pulping, pre-treatment of biomass, hydrogenolysis, acid-catalyzed treatment, base-catalyzed treatment, or combination of two or more thereof.

19. A method of coating an article with a lignin derivative, wherein the method comprises contacting an article with one or more groups of Formula I:

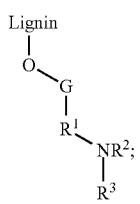

wherein:
G is absent or a polymeric group;
R¹ is an alkylene, (alkyleneamino)$_q$, (alkyleneoxy)$_q$, (alkyleneoxyarylene or (alkyleneoxyarylene)alkylene(aryleneoxyalkylene)$_q$ moiety, wherein q is from 1 to 10;
R² is H or alkyl;
R³ is a polycation; and
the Lignin is a lignin product derived from a process comprising extraction of finely ground wood, acidic dioxane extraction of wood, steam explosion, dilute acid hydrolysis, ammonia fiber expansion of a biomass, pulping of lignocellulosics, hydrogenolysis of lignin, the acid-catalyzed or base-catalyzed treatment of lignin, or combination of two or more thereof.

20. The method of claim 19, wherein the article is a packaging, pharmaceutical, cosmetic, perfume, thermoplastic, garment, paper product, drywall, medical equipment, or toy.

21. The method of claim 19, wherein Lignin-OGR¹— is a group of formula:

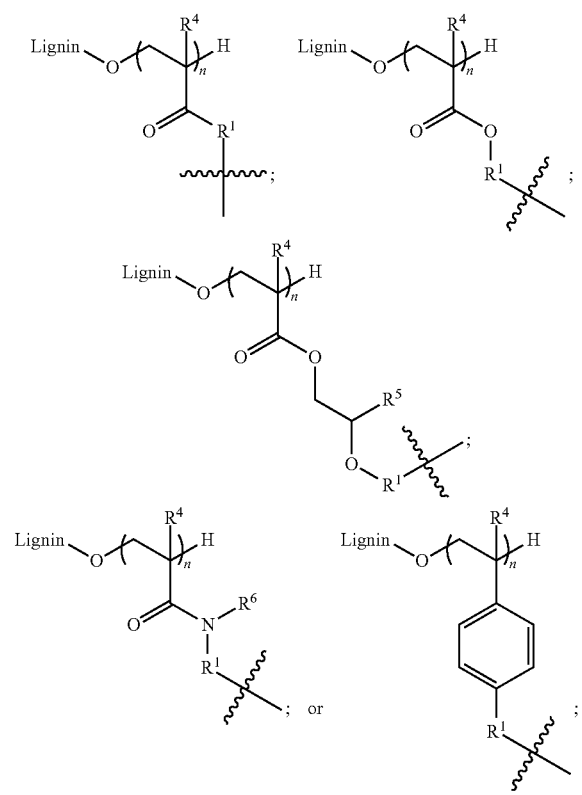

wherein:
R⁴ is H, alkyl, alkenyl, alkynyl, alkoxy, ester, or CN;
R⁵ is H or alkyl;
R⁶ is H or alkyl;
n is from 1 to 1000; and
the Lignin is a lignin product derived from a process comprising extraction of finely ground wood, acidic dioxane extraction of wood, steam explosion, dilute acid hydrolysis, ammonia fiber expansion of a biomass, pulping of lignocellulosics, hydrogenolysis of lignin, the acid-catalyzed or base-catalyzed treatment of lignin, or combination of two or more thereof.

22. The lignin derivative of claim 1, wherein the lignin is derived from hydrogenolysis of lignin, the acid-catalyzed treatment of lignin, or the base-catalyzed treatment of lignin.

* * * * *

UNITED STATES PATENT AND TRADEMARK OFFICE
CERTIFICATE OF CORRECTION

PATENT NO.       : 9,095,142 B2
APPLICATION NO.  : 13/812402
DATED            : August 4, 2015
INVENTOR(S)      : Gu It is certified that error appears in the above-identified patent and that said Letters Patent is hereby corrected as shown below:

In the specification

In Column 1, Lines 29-30, delete "biopolymer earth" and insert -- biopolymer on earth --, therefor.

In Column 1, Line 51, delete "fit some" and insert -- in some --, therefor.

In Column 2, Line 18, delete "any of" and insert -- any of the --, therefor.

In Column 4, Line 40, delete "or an" and insert -- or aryl --, therefor.

In Column 4, Line 66, delete "hydroxyalkyl," and insert -- haloalkyl, hydroxyalkyl, --, therefor.

In Column 5, Lines 3-4, delete "cycloalkenyl)cycloheteroalkyls" and insert -- cycloalkenyl), cycloheteroalkyls --, therefor.

In Column 5, Line 44, delete "lysine ornithine," and insert -- lysine, ornithine, --, therefor.

In Column 5, Line 62, delete "acids such" and insert -- acids, such --, therefor.

In Column 8, Line 4, delete "with in" and insert -- with an --, therefor.

In Column 8, Line 63, delete "$R^2$ is 11" and insert -- $R^2$ is H --, therefor.

In Column 10, Line 45, delete "polycations, in" and insert -- polycations. In --, therefor.

In Column 11, Line 21, delete "Formula $G^1$" and insert -- Formula I, $G^1$ --, therefor.

In Column 11, Line 24, delete "$R^2$ is" and insert -- $R^2$ is H --, therefor.

Signed and Sealed this
Twenty-second Day of March, 2016

Michelle K. Lee
*Director of the United States Patent and Trademark Office*

CERTIFICATE OF CORRECTION (continued)
U.S. Pat. No. 9,095,142 B2

In the specification

In Column 11, Line 62, delete "growth observed" and insert -- growth is observed --, therefor.

In Column 12, Line 30, delete "$R^2$ is H" and insert -- $R^2$ is H or --, therefor.

In Column 16, Line 33, delete "that were" and insert -- that where --, therefor.

In Column 18, Line 10, delete "it is" and insert -- It is --, therefor.

In Column 18, Line 25, delete "imitation," and insert -- limitation, --, therefor.

In Column 19, Line 9, delete "as will be" and insert -- Finally, as will be --, therefor.